United States Patent [19]

Fichet

[11] Patent Number: 5,523,234
[45] Date of Patent: Jun. 4, 1996

[54] EQUIPMENT FOR THE ANAEROBIC FERMENTATION OF ORGANIC MATERIALS

[75] Inventor: Georges Fichet, Antony, France

[73] Assignee: Gaz de France, Paris, France

[21] Appl. No.: 262,084

[22] Filed: Jun. 17, 1994

[30] Foreign Application Priority Data

Jun. 23, 1993 [FR] France .................................. 93 07648

[51] Int. Cl.[6] .................................................. C12M 3/00
[52] U.S. Cl. .................................... 435/289.1; 435/290.1; 435/290.2; 435/290.4; 435/813; 435/818
[58] Field of Search ........................... 422/231; 435/313, 435/316, 801, 813, 818, 290.1, 290.2, 290.4, 289.1, 813, 818

[56] References Cited

U.S. PATENT DOCUMENTS 4,036,699  7/1977  Quigg ...................................... 195/142

FOREIGN PATENT DOCUMENTS

| 0250998 | 6/1987 | European Pat. Off. . |
| 914808 | 8/1944 | France . |
| 63-084693 | 4/1988 | Japan . |
| 2189237 | 3/1986 | United Kingdom . |

Primary Examiner—David A. Redding
Attorney, Agent, or Firm—Pennie & Edmonds

[57] ABSTRACT

An equipment for the anaerobic fermentation of organic materials, which includes a plurality of nozzles for injecting biogas under pressure into a fermenter, which nozzles are fitted on the periphery of the fermenter to improve the flow of the materials within this fermenter as well as its efficiency and are fed with biogas by a pipeline shaped as two half-rings surrounding the fermenter and connected to a biogas supply, the equipment solving the problems of transit and fermentation of organic materials within fermenters with a large volume.

8 Claims, 2 Drawing Sheets

5,523,234

EQUIPMENT FOR THE ANAEROBIC FERMENTATION OF ORGANIC MATERIALS

TECHNICAL FIELD

The present invention relates essentially to an improved equipment for the anaerobic fermentation of organic materials derived for instance from town refuse or trash such as garbage or household refuse.

BACKGROUND ART

It is for a long time that equipments for the anaerobic fermentation of organic materials essentially comprise a fermenter in which the organic materials are caused to stay for some time with a view in particular to produce biogas.

The fermenter however, especially when it exhibits a substantial volume, raises problems of flow of the materials it contains.

In fermenters with a large volume indeed many rheologic phenomena occur in the vicinity of the introduction of the material as well as in respect of their transiting in the fermenters.

During the time of residence of the material within the fermenter, it is very difficult, even with the assistance of a vertical injection through the body of material within the fermenter, of biogas recycled and intended to displace this body of material from the inlet towards the outlet of the fermenter, to retain a homogenous viscosity within the whole bulk of this body of material.

In the peripheral zones inside of the fermenter there in particular remain amounts of material difficult to be kept under control.

Within these areas owing to the immovability of the material the viscosity would evolve with respect to the remainder of the medium, shearings would occur in the layers and it results therefrom a segregation of the different components. The heaviest particles would travel towards the bottom of the fermenter and create a deposit.

Such a sedimentation, if nothing is done, would be irreversible and evolving. The deposits would be increasing and continuously reduce the active volume of the fermenter and therefore its efficiency.

Since a fermenter is put in operation for many years, it is of prime importance to control this phenomenon, i.e. in short to solve the problem of the flow of the materials within the fermenters especially when the latter exhibits a large volume.

The present invention reaches this goal.

SUMMARY OF THE INVENTION

The invention relates to an improved equipment for the anaerobic fermentation of organic materials such for example as household refuse, garbage or trash within a fermenter where the said materials are staying for some time with the view to produce biogas in particular, characterized by a plurality of nozzles for the injection under pressure of biogas and/or other gaseous, liquid or more or less solid materials into the fermenter, which nozzles are distributed around the periphery of the fermenter in same plane or in different planes to thereby improve the flow of the materials within the fermenter and its efficiency.

According to another characterizing feature of this equipment, the injection nozzles are connected through one valve to at least one ring-shaped pipeline surrounding the fermenter and itself connected to at least one supply duct According to a preferred embodiment this equipment is characterized in that the aforesaid pipeline forms two half rings each half-ring having two ends, one of which is joined to one end of the other half-ring thus provide a connecting zone comprising two valves between which is connected the aforesaid supply duct.

This equipment is further characterized in that some injection nozzles are set substantially normally into the wall of the fermenter whereas other nozzles are set in on the wall of the fermenter along directions which are not perpendicular to the said wall.

According to still another characterizing feature of the invention, the fermenter, being of a circular cylindrical shape, comprises several groups of injection nozzles located in at least one cross-sectional plane of the fermenter, namely:

a first group of nozzles set in on the external wall of the fermenter symmetrically on either side of a first diameter of the fermenter at a distance from this diameter equal to one third of the radius of the fermenter, the axes of these nozzles being directed radially;

a second group of nozzles set in on the external wall of the fermenter symmetrically on either side of a second diameter of the fermenter perpendicular to the first diameter, the axes of these nozzles forming an angle of about 15° with the centrifugal direction of the second diameter; and a third group of nozzles set in on the external wall of the fermenter at the point of intersection of the wall with a straight mid-perpendicular line of the radius of the first diameter, the axis of each nozzle of this third group coinciding with the chord of the arc of wall connecting the said nozzle to the neighboring nozzle of the first group of nozzles.

The equipment of this invention is further characterized in that the aforesaid supply duct feeding the half-rings connected to the nozzles is fed with biogas by at least one tank or vessel connected to a compressor.

BRIEF DESCRIPTION OF THE DRAWINGS

The invention will be better understood and further objects, characterizing features, details and advantages thereof will appear better as the following explanatory description proceeds with reference to the accompanying diagrammatic drawings given by way of non-limiting example only illustrating a presently preferred specific embodiment of the invention and in which.

DETAILED DESCRIPTION OF THE INVENTION

Figure 1:
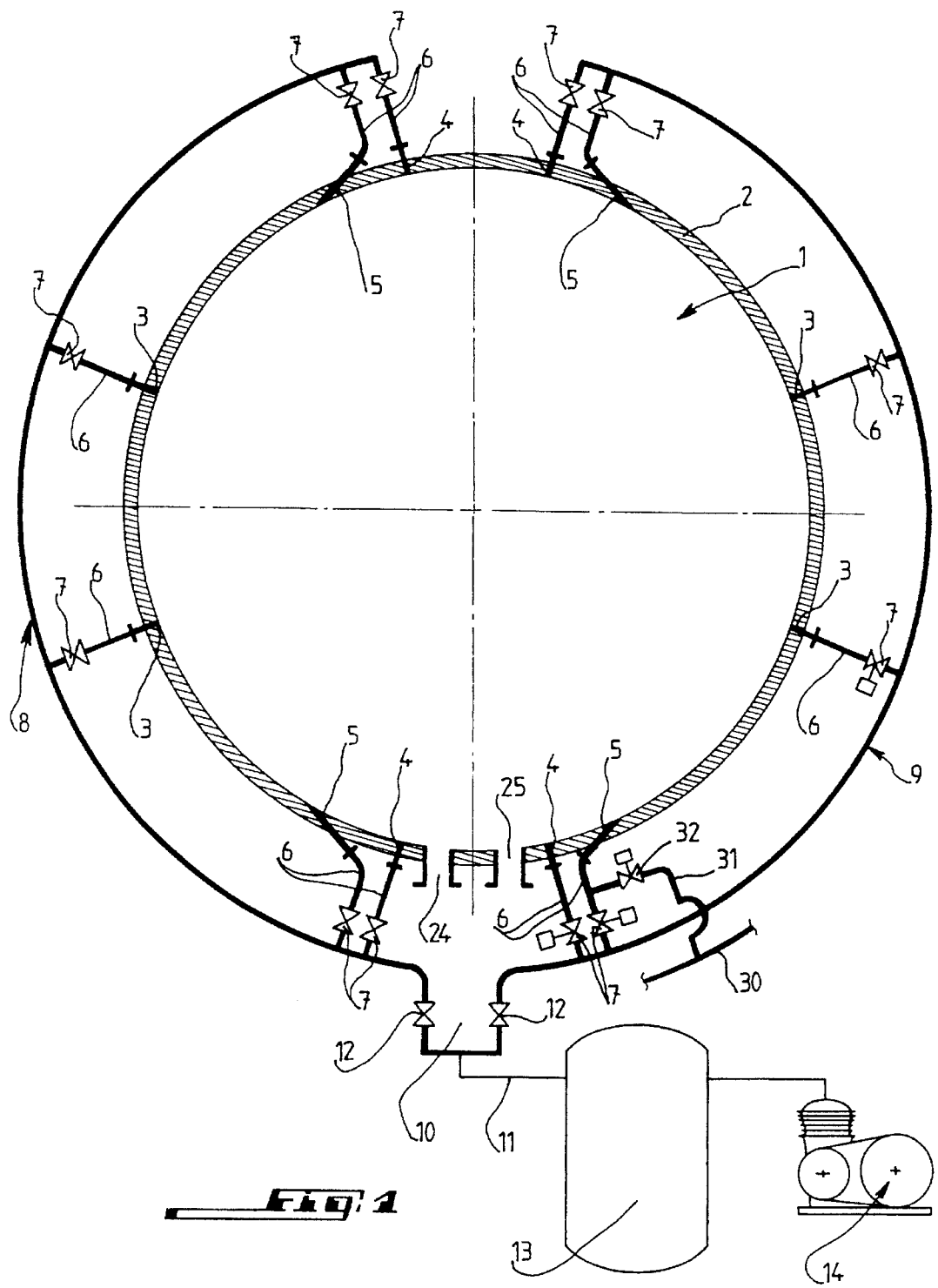
FIG. 1 is a diagrammatic view in cross-section of a fermenter fitted with means according to this invention.

Referring more particularly to FIG. 1, there is shown an anaerobic fermentation equipment consisting essentially of a fermenter or digester 1 into which may be introduced organic materials which would stay therein for some time and the fermentation of which permits to produce biogas.

According to the invention, a plurality of nozzles 3, 4, 5 for the injection under pressure of biogas and/or other gaseous, liquid or more or less solid materials are fitted into the external wall 2 of the fermenter 1.

Some of these nozzles such as the nozzle 3 are fitted substantially normally to the wall 2 of the fermenter whereas other nozzles such as the nozzles 4 and 5 are fitted on the wall 2 of the fermenter 1 along directions which are not normal to the wall 2.

As it clearly appears from FIG. 1, the injection nozzles 3, 4, 5 made fast to the wall 2 of the fermenter 1 are connected through the agency of a duct 6 having a valve 7 to a pipeline shaped as two half-rings 8, 9 surrounding the fermenter 1.

More specifically both half-rings 8, 9 are joined by one only of their ends to thus form a connection zone 10 provided with two valves 12. Between these two valves is connected a duct 11 for feeding recycled biogas under pressure. The duct 11 is connected to a tank or vessel itself supplied with biogas by a compressor 14. Thus the tank 6 would store biogas until obtaining the required pressure in the half-rings 8, 9 supplying gas to the injection nozzles 3, 4, 5 through the ducts 6.

In some working circumstances, it may be advantageous without departing from the scope of the invention to use instead of biogas, fresh organic material or organic material taken from another fermenter, this material being of course capable of being injected into the fermenter 1 through the nozzles 3, 4, 5. Such a material could be injected for example through the medium of a ring 30 independent of the pipeline 8, 9 and connected to a duct 31 provided with a valve 32 communicating with one nozzle or some nozzles such as 5.

This solution allows to restore a momentary drift of the homogeneousness of the whole material within the digester 1 and in particular within the internal peripheral zones of the digester. It will therefore be possible to use either a system with a tank 13 and compressor 14 for the supply or another system in accordance with the material to be injected into the digester to solve the problems of flow and of transit or conveyance of the said material within the digester, especially when the latter exhibits a large volume.

The injection nozzles 3, 4, 5 may have a well determined orientation in accordance with the material injected by the nozzles and with the operating conditions as subsequently described in detail.

The valves 7 upstream of the injection nozzles 3, 4, 5 connected by the ducts 6 to the half-rings 8, 9 may be controlled from an automaton or other programming apparatus (not shown) according to a suitable sequence which may vary according to the viscosity of the fermentable material. Such a sequence could be carried out when recycled biogas is used as an injection material as well as when a fresh organic material or materials with an intermediate degradation level taken from another digester are used.

The injection nozzles 3, 4, 5 are of course judiciously oriented so as to permit a homogenization of the whole material being fermenting within the digester 1.

Moreover they may be in any number whatsoever and they may be distributed over the periphery of the digester 1 in a same plane or in different planes over the whole height of the digester. This means in the latter case that the half-rings 8, 9 assembled as previously explained may be arranged on several levels along the height of the fermenter 1, it being understood that the provision of half-rings with associated injection nozzles in the lower portion of the fermenter 1 remains the most important one since it is there where the risks of sedimentation are the most marked.

Instead of one pipeline consisting of two half-rings 8, 9 joined as shown on FIG. 1 and which opposite to the connection zone 10 exhibits an interruption, it would be perfectly possible without leaving the scope of the present invention to use a pipeline shaped as one single ring fully surrounding the external wall 2 of the fermenter 1.

Figure 2:
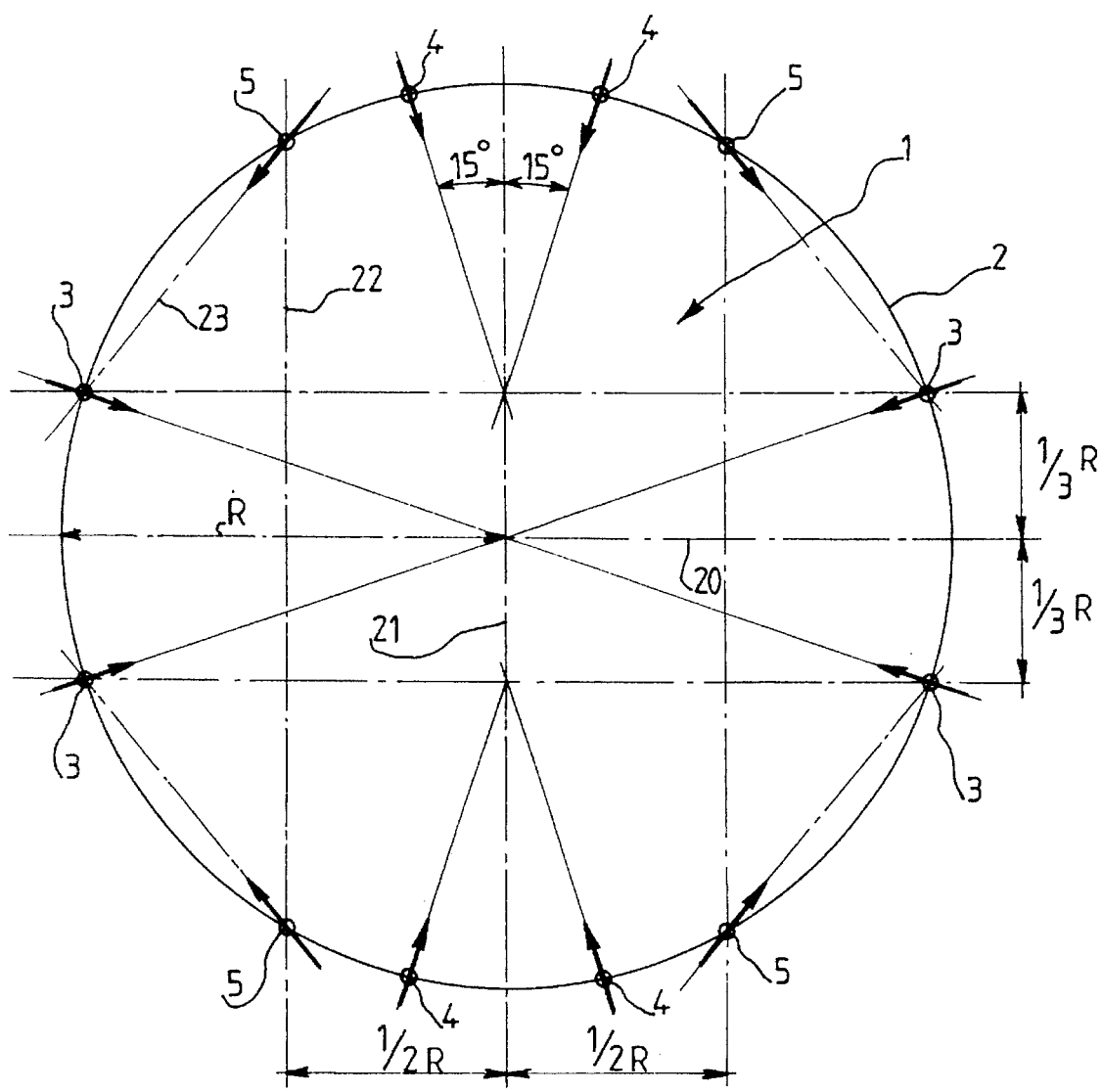
FIG. 2 is a likewise diagrammatic view in cross-section of the fermenter illustrating the position and orientations of the injection nozzles according to an exemplary embodiment.

Reference should now be had to FIG. 2 which clearly illustrates an exemplary embodiment of fitting of the injection nozzles 3, 4, 5 into the wall 2 of the fermenter 1 and this in a cross-sectional plane of the said fermenter.

The injection nozzles 3, 4, 5 form three groups of nozzles fitted and oriented in the following manner.

The first group consists of four nozzles 3 which are fitted on the wall 2 of the digester 1 symmetrically on either side of a first diameter 20 of the fermenter and at a distance from this diameter 20 equal to one third of the radius R of the fermenter. As it is well seen on the figure the axes of the nozzles 3 are directed radially.

The second group consists of four nozzles 4 which are fitted in on the wall 2 symmetrically on either side of a second diameter 21 of the fermenter perpendicular to the first diameter 20. The axes of these nozzles form an angle of 15° with the centrifugal direction of the second diameter 21.

At last the third group of nozzles consists of four nozzles 5 fitted on the wall 2 of the fermenter at the point of intersection of a straight line 22 which is the mid-perpendicular to the radius of the first diameter 20. As well seen on FIG. 2 the orientation or the axis of each nozzle 5 coincides with the chord 23 of the arc of wall 2 connecting one nozzle 5 to an adjacent nozzle 3 of the first group.

According to this example of fitting there are used twelve injection nozzles four of which, namely the nozzles 3 are directed radially whereas the eight of the nozzles are more or less inclined.

It would however be perfectly possible to use another number of injection nozzles with different orientations and this in several planes distributed over the height of the fermenter without departing from the scope of the invention.

The fermenter 1 may be a fermenter with a substantial volume and comprise as shown at 24 and 25 on FIG. 1 one inlet and one outlet for the material as well as a partition wall (not shown) coinciding with the second diameter 21 having its root on the internal periphery of the fermenter 1 between the inlet 24 and the outlet 25 and extending over one portion only of the second diameter 21.

The invention is of course not at all limited to the embodiment described and shown which has been given by way of example only.

Thus the injection nozzles may have any positions and orientations whatsoever which are a function of the dimensions of the fermenter and of the nature of the materials to be treated. Likewise the half-rings with injection necks or pipe runs may be in any number whatsoever as well as the type of valves used upstream of the injections on condition that the opening, the opening time and the closing of these valves may be operated according to any sequence whatsoever by a programmable automatic device or the like. The injection nozzles are also of any suitable design whatsoever and adapted to allow the injection of gases, liquids or even of more or less solid materials.

This means that the invention comprises all the technical equivalents of the means described as well as their combinations if the latter are carried out according to its gist and within the scope of the appended claims.

What is claimed is:

1. An improved fermenter for the anaerobic fermentation of organic materials comprising:

a plurality of nozzles for the injection of a biogas under pressure into the fermenter, which nozzles are distributed around the periphery of the fermenter to thus improve the flow of the organic materials in the fermenter and its efficiency;

wherein the injection nozzles are connected through one valve to at least one ring-shaped pipeline surrounding the fermenter and the pipeline is connected to at least one supply duct; and wherein the pipeline forms two half-rings, each half-ring having two ends, one of which is joined to one end of the other half-ring to thereby constitute a connecting zone comprising two valves between which the supply duct is connected.

2. An equipment according to claim 1, wherein some injection nozzles are fitted substantially normally to the wall of the fermenter whereas other nozzles are fitted on the wall of the fermenter along directions which are not normal to the said wall.

3. An equipment according to claim 1, wherein the fermenter being of circular cylindrical shape comprises several groups of injection nozzles located in at least one cross-sectional plane of the fermenter, namely:

a first group of nozzles fitted on the external wall of the fermenter symmetrically on either side of a first diameter of the fermenter at a distance from this diameter equal to one third of the radius of the fermenter, the axes of these nozzles being directed radially;

a second group of nozzles fitted in on the external wall of the fermenter symmetrically on either side of a second diameter of the fermenter perpendicular to the first diameter, the axes of these nozzles forming an angle of about 15° with the centrifugal direction of the second diameter; and a third group of nozzles fitted in on the external wall of the fermenter at the point of intersection of the wall with a straight line forming a midperpendicular to the radius of the first diameter, the axis of each nozzle of this third group coinciding with the chord of the arc of wall connecting the said nozzle to the adjacent nozzle of the first group.

4. An equipment according to claim 1 wherein the aforesaid supply duct is fed with biogas by a tank connected to a compressor.

5. An improved equipment for the anaerobic fermentation of organic materials such for instance as household refuse in a fermenter where the said materials are staying for some time with a view in particular to produce biogas, wherein the improvement consists of a plurality of nozzles for the injection of biogas and/or other gaseous, liquid or more or less solid materials under pressure into the fermenter, which nozzles are distributed over and made fast to the periphery of the fermenter in a same plane or in different planes to thus improve the flow of the materials in the fermenter and its efficiency, and said injection nozzles are connected through the medium of one valve to at least one ring-shaped pipeline surrounding the fermenter and itself connected to at least one duct for the supply with recycled biogas or with another material, and the pipeline forms two half-rings each half-ring having two ends only one of which is joined to one end of the other half-ring to thereby constitute a connecting zone comprising two valves between which the aforesaid supply duct is connected.

6. An equipment according to claim 5, wherein some injection nozzles are fitted substantially normally to the wall of the fermenter whereas other nozzles are fitted on the wall of the fermenter along directions which are not normal to the said wall.

7. An equipment according to claim 5, wherein the fermenter being of circular cylindrical shape comprises several groups of injection nozzles located in at least one cross-sectional plane of the fermenter, namely:

a first group of nozzles fitted on the external wall of the fermenter symmetrically on either side of a first diameter of the fermenter at a distance from this diameter equal to one third of the radius of the fermenter, the axes of these nozzles being directed radially;

a second group of nozzles fitted in on the external wall of the fermenter symmetrically on either side of a second diameter of the fermenter perpendicular to the first diameter, the axes of these nozzles forming an angle of about 15° with the centrifugal direction of the second diameter; and a third group of nozzles fitted in on the external wall of the fermenter at the point of intersection of the wall with a straight line forming a mid-perpendicular to the radius of the first diameter, the axis of each nozzle of this third group coinciding with the chord of the arc of wall connecting the said nozzle to the adjacent nozzle of the first group.

8. An equipment according to claim 5, wherein the aforesaid supply duct is fed with biogas by a tank connected to a compressor.

* * * * *